(12) United States Patent
Corzani

(10) Patent No.: US 6,933,420 B1
(45) Date of Patent: Aug. 23, 2005

(54) DOPED ODOR CONTROLLING MATERIALS

(75) Inventor: Italo Corzani, Chieti (IT)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/622,381

(22) PCT Filed: Feb. 2, 1999

(86) PCT No.: PCT/IB99/00185

§ 371 (c)(1),
(2), (4) Date: Aug. 16, 2000

(87) PCT Pub. No.: WO99/40953

PCT Pub. Date: Aug. 19, 1999

(30) Foreign Application Priority Data

Feb. 17, 1998 (EP) ............................................. 98102691

(51) Int. Cl.⁷ ............................................... A61F 13/15
(52) U.S. Cl. ....................................... 604/359; 604/360
(58) Field of Search ................................. 423/700–718; 604/359, 360, 367; 23/300, 295, 313, 314

(56) References Cited

U.S. PATENT DOCUMENTS

| 3,939,838 | A | * | 2/1976 | Fujinami et al. ............. 604/359 |
| 4,296,083 | A | * | 10/1981 | Rollmann ................... 423/708 |
| 4,539,191 | A | * | 9/1985 | Kostinko .................... 423/275 |
| 4,806,327 | A | * | 2/1989 | Rieck et al. ................ 423/332 |
| 5,407,442 | A | * | 4/1995 | Karapasha ................... 424/688 |
| 5,635,196 | A | * | 6/1997 | Murphy ...................... 424/409 |
| 5,733,272 | A | * | 3/1998 | Brunner et al. ............. 604/359 |
| H1732 | H | * | 6/1998 | Johnson ........................ 428/68 |
| 5,864,923 | A | * | 2/1999 | Rouanet et al. ................ 23/295 |
| 5,914,184 | A | * | 6/1999 | Morman ................ 428/385.19 |
| 5,944,704 | A | * | 8/1999 | Guarracino et al. ......... 604/359 |
| 5,951,534 | A | * | 9/1999 | Cummings et al. ......... 604/359 |
| 6,284,218 | B1 | * | 9/2001 | Kuvettu et al. ............. 423/709 |
| 6,616,910 | B2 | * | 9/2003 | Rouleau et al. ............. 423/706 |

FOREIGN PATENT DOCUMENTS

| EP | 0 103 214 A2 | 3/1984 |
| WO | WO 81/01643 | 6/1981 |

* cited by examiner

Primary Examiner—Larry I. Schwartz
Assistant Examiner—C. Lynne Anderson
(74) Attorney, Agent, or Firm—Leonard W. Lewis; Theodore P. Cummings

(57) ABSTRACT

An odor controlling material and an absorbent article containing material for removing or reducing odor emanating from certain gaseous and liquid compounds in body fluid. The odor controlling material includes conventional absorbent materials such as silica, alumina, silicates, and natural and synthetic aluminosilicates that are doped with one or more dopants, which have the same or similar chemical characteristics as the gaseous or liquid compounds in the body fluid to be absorbed. These dopants include fatty acids and their derivatives, amines and their salts, ammonia, alcohols, aldehydes, ketones, heterocompounds containing at least one nitrogen, sulfur or oxygen atom and mixtures thereof. The odor control material is suitable for incorporation in an absorbent article such as a pantiliner or a sanitary napkin.

14 Claims, No Drawings

DOPED ODOR CONTROLLING MATERIALS

This invention relates to an odour controlling material, and in particular to articles such as absorbent articles for absorbing bodily fluids, comprising the odour controlling material and to the use of an adsorbent material as an odour controlling material.

Malodours may be present in the environment from numerous sources both animate and inanimate. Many products and articles are available which aim to avoid or minimize the detection of such odours. This includes ventilation systems, room freshners, car freshners, and animal litter, for example. Indeed it is particularly desirable to provide odour controlling materials to address the malodours which are generated by the human body, or from bodily fluids such as perspiration, bad breath, urine, faeces, menstrual fluids and the like.

Absorbent articles for example are designed to be worn by humans to absorb bodily fluids, such as urine, menstrual fluid and perspiration, etc. Examples of absorbent articles include sanitary napkins, pantiliners, disposable diapers, incontinence pads, tampons, perspiration pads and the like.

In use, the absorbent articles are known to acquire a variety of compounds, for example volatile fatty acids (e.g. isovaleric acid), ammonia, amines (e.g. triethylamine), sulfur containing compounds (e.g. mercaptans, sulphides), which release unpleasant odours. These compounds may be present in the bodily fluid or may be produced by fermentation once the bodily fluid is absorbed into the pad. In addition bodily fluids can contain microorganisms that can also generate malodorous by products. Unpleasant odours which emanate from absorbent pads when in use may make the wearer feel self conscious.

Various odour controlling materials have been disclosed. In particular, certain zeolitic materials are becoming known for their odour controlling properties. Zeolitic materials are generally quite safe and have been found to control many odours associated with bodily fluids.

For example U.S. Pat. No. 4,304,675 discloses a powdered carpet treatment composition containing a natural or synthetic zeolite, preferably zeolite A. U.S. Pat. No. 4,525,410 discloses a fiber article having antibacterial properties comprising zeolitic particles retaining therein at least one metal ion having bactericidal property and a mixed fiber assembly.

WO 81/01643 discloses the removal of ammonia and other toxic or potentially toxic nitrogenous irritants from diapers by incorporating into the diaper an inorganic aluminosilicate zeolite ammonium ion exchange material.

Active silica is also a known adsorbent material which is very efficient in extracting and storing various chemical species both from the liquid and gaseous phases.

In many applications, however, it would be desirable to enhance the adsorption power of the material, such as active silica, both in general terms and, specifically, in terms of selectivity with regard to particular chemical compounds. For example, in the case of hygienic articles containing an adsorbent material such as active silica or zeolite for adsorbing malodorous chemical species contained or generated in the physiological fluids.

Such malodorous compounds can be classified in various chemical groups such as low molecular weight fatty acids; ammonia and amines; alcohols, ketones and aldehydes; and heterocompounds particularly those containing sulfur or nitrogen atoms. Many of these compounds generate an extremely powerful odour which can clearly be detected by human olfaction even in amounts of a few parts per billion.

It is an object of the present invention to improve the adsorption power of these known adsorbent materials and specifically to improve their selectivity with regard to specific adsorbing power verses selected compounds.

According to the present invention there is provided an odour controlling material for removing or reducing odour emanating from certain gaseous or liquid compounds which comprises an inorganic adsorbent material doped with one or more dopants which are selected from the gaseous or liquid compounds and derivatives thereof, and compounds belonging to the same chemical class or having similar functionalities.

The adsorbent material may be, for example, silica, specifically active silica, alumina, silicates and natural and synthetic aluminosilicates such as zeolites, e.g. zeolite A.

By the present invention it has been surprisingly discovered that the adsorption capability of adsorbent materials can be significantly improved by doping with trace amounts of doping impurities which are selected from those compounds which have to be adsorbed or derivatives thereof or compounds of the same chemical class or having similar functionalities. These doping impurities can be broadly selected from fatty acids and derivatives thereof; ammonia and amines and their salts; alcohols, aldehydes and ketones; and heterocompounds.

The fatty acids are volatile fatty acids selected from straight chain and branched chain fatty acids containing, for example, from 1 to 12 carbon atoms, for example isovaleric acid. Another class of odorous compounds include ammonia and ammonium salts and amines having a boiling point of up to 170° C. at atmospheric pressure and salts thereof, e.g. triethylamine.

A further class of odorous compounds comprises alcohols, aldehydes such as furaldehyde, and ketones having a boiling point of up to 170° C. at atmospheric pressure.

Another class of odorous materials include heterocompounds containing at least one nitrogen, sulfur or oxygen atom, preferably heterocyclic compounds containing one or two cyclic rings and containing one or two heteroatoms which may be the same or different. Other compounds in this category include mercapto- and thio-compounds and other compounds containing at least one sulphur atom per molecule which have a boiling point up to 170° C. at atmospheric pressure.

According to the invention the doping impurity can be one of the malodorous compounds which has to be adsorbed. Alternatively, the doping impurity can be a derivative, such as a salt or ester, of the malodorous compound to be adsorbed. According to a further possibility the doping impurity can be a compound of the same chemical class or having the same functionalities as the compound to be adsorbed. For example, if valeric acid is the compound to be adsorbed the doping impurity can be any low molecular weight fatty acid such as butyric acid.

We have found that the improved adsorption is achieved with very small traces of the specific doping impurity or doping impurities. Concentrations of from 1 to 1000 parts per million by weight have been demonstrated to show significantly increased adsorbing power. Moreover, this improvement has been found to apply to the general adsorption power of the doped adsorbent material and also the selective adsorption in relation to specific classes of chemical compounds. A preferred concentration range is from 3 to 100 parts per million by weight and preferably from 10 to 50 parts per million by weight.

According to the present invention the adsorbent material can be doped with a number of different Impurities or dopants selected from the same or different classes of compound. We have found that there are particular benefits in using a dopant which has more than one active group e.g. ammonium butyrate which has both acid and ammonium groups. Such dopants may provide a synergy over two separate classes of compounds used as dopants.

According to one embodiment of the invention the adsorbent material is used at a neutral pH i.e. pH of 7±0.5. However, according to other embodiments of the invention the pH of the adsorbent material can be adjusted according to the polar character of the malodorous substances. It is known that a strongly acid or a strongly basic adsorbent material, e.g. active silica, can be prepared to show an increased adsorbing power respectively with regard to basic and acid substances. However, this apparent higher adsorption is not a true adsorbent capability but is based on a chemical reaction so that the effect is transitory i.e. it is maintained only until the excess acidity or basicity, available for reaction, has been neutralized.

When the odour controlling material of the present invention is used for feminine hygiene, for example incorporated in a pantiliner or a sanitary napkin, it is preferred to provide the material with a neutral pH because malodorous compounds present in physiological fluids may be acidic, basic or neutral.

When used in other absorbent articles where the malodours have a defined and constant character, e.g. ammonia and amines originating from urine, the pH can be adjusted, in this case to an acidic pH to provide supplementary odour control to that provided by the doping impurities.

The doped adsorbent material can be prepared by any convenient known method. For example in the case of an adsorbent material comprising silica, silicagel or active silica can be prepared by precipitation as a gel from a solution of a soluble silicate by addition of an acid, such as sulphuric acid, or by flocculation of a colloidal solution of silica.

For example, the selected dopant or dopants are added to a solution of a soluble silicate at a temperature of, e.g. between 40 and 100° C., preferably between 60 and 95° C. Sulphuric acid is added and the pH adjusted as required, preferably to a neutral pH. The mass is preferably maintained at a temperature of 60 to 95° C. for a period of 10 to 30 minutes prior to the addition of a flocculant where the solution is a colloidal solution, followed by filtration or centrifugation and drying to yield the doped materials.

Conventional flocculating agents, which may be organic or inorganic, can be employed. Organic agents are preferred and especially Poly(ethylene oxide) polymers having molecular weights higher than 100,000 Daltons; polyethylene imine; surfactants such as benzalkonium and betaine derivatives.

Soluble silicates that are particularly useful as raw materials according to the present invention are those which, in the anhydrous form, may be described by the general formula: $Me_2O.nSiO_2$ where $0.5 £ n £ 4$ and Me is an alkali metal. We have found that the improved adsorbent properties are achieved independently of the method of production of the adsorbent material, e.g. active silica.

The pH of the material can be adjusted as desired. After drying, the resulting substantially amorphous silica retains an extremely porous structure even in the anhydrous state. The porous structure contributes to the adsorbing capability of the material towards both gaseous and liquid molecules.

The gelation or the formation of the colloidal solution of silica takes place, according to the present invention, in the presence of traces of the specific doping impurities e.g. in concentrations of from 1 to 1000, preferably 3 to 100 and most preferably 10 to 50 parts per million by weight.

The precipitates or gels of silica are dried until constant weight at a temperature between 80 and 1000° C., more preferably between 110 and 500° C. and most preferably between 150 and 250° C.

The invention is illustrated by reference to the following Examples and Comparative Examples.

A reference active silica (DG 14) was prepared by the Gel process and dried at 190° C. Final pH was 7.10.

All other silica samples were prepared under the same conditions apart from the addition of selected doping impurities.

In the comparison of various active silicas for adsorbing power, two silicas were tested in parallel by flowing on them a stream of nitrogen containing a known concentration of a malodorous compound and measuring the adsorbed percent of that compound. The test method used was as follows:

Test Method

A glass cup was put in the bottom of a glass vessel of total volume of about 250 milliliters. The glass cup contained:
  0.5 grams of active silica under test
  0.5 grams of the "reference" malodorous compound solution i.e. a 2% by weight water solution of butyric acid or a 5% b.w. solution of trimethylamine.
  Both solutions were buffered by adding=0.01 M of phosphate buffer, 0.0027 M of potassium chloride and 0.137 M of sodium chloride with an average pH=7.4.

A glass small pipe entered into the vessel arriving at about 1 cm over the blend of active silica and the above solution; through this glass pipe was flowing nitrogen at a flow rate regulated between 15 and 20 milliliters/minute.

The gas escaping from the vessel was passed through a "Draeger Tube" available from National Draeger Inc (USA) and used to adsorb and measure specific impurities contained as mixed gases or vapours in a main gas stream.

In particular, when the malodorous compound, was butyric acid we used as detector the Draeger tube 67 22101 whose scale is conventionally expressed in ppm of adsorbed acetic acid (kept as a reference material for volatile low molecular weight acids); while when the malodor was trimethylamine, we used the Draeger tube CH 20501 whose scale is conventionally expressed in ppm of adsorbed ammonia. The test is performed at 23° C.

It is clear that in any case the adsorption activity of the tested silica is inversely proportional to the malodorous compound detected by the Draeger tube.

In particular the adsorption ability of the tested active silica is kept inversely proportional to the quantity of malodourant compound escaped from the solution and detected by the Draeger tube after that a fixed flow rate of contaminated nitrogen has passed through the tube. Owing to the different capacity and sensitivity of the two used Draeger tube types, the reading of detected malodourant compound was made at different timings for butyric acid and for trimethylamine. More precisely, after having reached a steady state of flow of nitrogen and after having recorded the actual gaseous flow, the timer is started. The reading of impurities adsorbed by the tube is made:
  after the passage of 300 milliliters of nitrogen (so between 15 and 20 minutes of test when testing for butyric acid)
  after the passage of 1000 milliliters of nitrogen (so between 50 and 67 minutes of test when testing for trimethylamine).

EXAMPLE 1

A doped active silica (DG 18) was prepared under the same conditions as DG 14 except that the gel was formed in the presence of 40 ppm of butyric acid. DG 14 and DG 18 were compared for activity in adsorbing malodorous low molecular weight fatty acids.

In the specific case they were tested as adsorption capability vs. the same butyric acid contained as vapour in a $N_2$ stream.

The result was that the doped material DG 18 had adsorbed 2.18 times more (+118%) than the undoped DG 14.

EXAMPLE 2

Another doped silica (DG 23) was prepared and tested for butyric acid adsorption under the same conditions except that the gel was formed in the presence of 19 ppm of $CH_3(CH_2)_2COOH$.

When compared with DG 14 the doped material DG 23, was shown to adsorb 13.3 times more volatile acid (+1230%).

EXAMPLE 3

A third silica doped with butyric acid (DG 30) was prepared in the presence of 10 ppm of impurity. This was compared with DG 23 for adsorption of acids and was found to have 2.6 times less activity than DG 23.

It can be extrapolated from these results that DG 30 is about 5.1 times more active (+410%) than DG 14. For doping with butyric acid and for the adsorption of volatile acids indicates an optimum value around a level of about 20 ppm of dopant.

EXAMPLE 4

For the adsorption of volatile acids, DG 23 was compared with a commercial active silica, SYLOBLANC 82 available from Grace Co. DG 23 was found to adsorb 3.7 times (+270%) more than SYLOBLANC 82.

It is noted that in the tested form, SYLOBLANC 82 has a bulk density which is more than 5 times lower than DG 23. So it would be expected that for this reason only SYLOBLANC 82 would have a much higher specific surface, active for adsorption, and that the comparative tests between SYLOBLANC 82 and DG 23 were not made under comparable conditions.

It is reasonable to expect that, if compared at the same bulk density, DG 23 would have shown an even higher advantage over the commercial material.

EXAMPLE 5

An active silica (DG 26) was doped with 32 ppm of tri-methylamine. When used for the adsorption of the same amine in comparison with the undoped DG 14, DG 26 was shown to adsorb 2.3 times more amine than the undoped material.

EXAMPLE 6

The same silica (DG 26) as in Example 5 was compared with another silica (DG 27) doped with 16 ppm of tri-methylamine. When compared for the adsorption of amines, looking for the optimum level of doping amine, bG 26 revealed to be twice as effective as DG 27.

A further surprising phenomenon was shown for DG 26. When tested for the adsorption of volatile acids DG 26 proved to be a very effective adsorber also for these materials even when the pH was neutral (pH=7.2).

All the above mentioned experiments show that it is possible to enhance the specific activity of an adsorbent active silica by doping it was traces of the same compound (or classes of compound) that must be preferentially adsorbed.

However, certain substances, such as tri-methylamine seem able to create an activation also versus other chemically different substances.

The present invention is not linked to any specific theory or supposed mechanism, but these results suggest that several mechanisms for achieving a higher and more selective adsorption capability are operable through the present method.

EXAMPLE 7

To confirm a possible synergy between different mechanisms, we prepared a silica (DG 32) doped with a compound having multifunctional groups.

The chosen compound was ammonium butyrate, because its molecule combines both types of supposed active groups investigated in these experiments.

It was added to the $SiO_2$ gel at a level of 20 ppm.

DG 32 was compared for adsorption of volatile acids with DG 23 (the previous best adsorber of acids, doped with 20 ppm of butyric acid).

It was actually found that DG 32 showed a further increase of adsorbing efficiency vs. DG 23 equal to +80% (1.8 times more).

What is claimed is:

1. An odor controlling material comprising, an adsorbent material, said adsorbent material being selected from the group consisting of silica, alumina, silicates, natural and synthetic aluminosilicates and mixtures thereof, said adsorbent material being doped with one or more dopants selected from the group consisting of fatty acids and their derivatives, ammonia and salts thereof, amines and salts thereof, alcohols, aldehydes, ketones, heterocompounds selected from the group consisting of heterocyclic compounds containing one or two heteroatoms selected from nitrogen, sulfur, and oxygen, mercapto-compounds, thio-compounds, and other compounds containing at least one sulfur atom per molecule and having a boiling point of up to 170° C. at atmospheric pressure, and mixtures thereof; wherein said dopant is present at from 1 to 1000 parts dopant per million parts of said adsorbent material.

2. An odour controlling material according to claim 1, wherein the adsorbent material is active silica.

3. An odor controlling material according to claim 2, wherein the fatty acids and their derivatives are selected from the group consisting of straight and branched chain fatty acids containing from 1 to 12 carbon atoms, and alkali and alkaline earth metal salts and their esters, ammonium salts, and amides thereof, and mixtures thereof.

4. An odour controlling material according to claim 1 which has a pH of 7±0.5.

5. An odour controlling material according to claim 1 which comprises at least one dopant which has more than one active group.

6. A blend of odour control materials comprising two or more odour control materials according to claim 1.

7. An absorbent article comprising at least one adsorbent material, said material selected from the group consisting of silica, alumina, silicates, natural and synthetic aluminosilicates and mixtures thereof, said material being doped with one or more dopants selected from the group consisting of fatty acids and their derivatives, amines and their salts, ammonia and salts thereof, alcohols, aldehydes, ketones, heterocompounds selected from the group consisting of heterocyclic compounds containing one or two heteroatoms selected from nitrogen, sulfur, and oxygen, mercapto-compounds, thio-compounds, and other compounds containing at least one sulfur atom per molecule and having a boiling point of up to 170° C. at atmospheric pressure; wherein said dopant is present at from 1 to 1000 parts dopant per million parts of said adsorbent material.

8. An absorbent article according to claim 7, wherein the material is active silica.

9. An absorbent article according to claim 8, wherein the fatty acids and their derivatives are selected from straight and branched chain fatty acids containing from 1 to 12 carbon atoms, and alkali and alkaline earth metal salts and their esters, ammonium salts, and amides thereof, and mixtures thereof.

10. An absorbent article according to claim 8, wherein the amines and their salts are selected from amines having a boiling point of up to 170° C. at atmospheric pressure.

11. An absorbent article according to claim 7 which has a pH of 7±0.5.

12. An absorbent article to claim 7 comprising at least one dopant, the dopant having more than one active group.

13. An absorbent article according to claim 7 comprising two or more of said materials.

14. An absorbent article according to claim 7 which is a pantiliner or a sanitary napkin.

* * * * *